United States Patent
Kumar et al.

(10) Patent No.: US 10,472,581 B2
(45) Date of Patent: Nov. 12, 2019

(54) PROCESS AND APPARATUS FOR HYDROCRACKING AND HYDROISOMERIZING A HYDROCARBON STREAM

(71) Applicant: UOP LLC, Des Plaines, IL (US)

(72) Inventors: Sailesh B. Kumar, Naperville, IL (US); Andrew J. Towarnicky, Park Ridge, IL (US); Vasant P. Thakkar, Elk Grove Village, IL (US); Massimo Sangalli, Des Plaines, IL (US); John A. Petri, Wauconda, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/621,791

(22) Filed: Jun. 13, 2017

(65) Prior Publication Data
US 2018/0002616 A1    Jan. 4, 2018

Related U.S. Application Data

(60) Provisional application No. 62/357,244, filed on Jun. 30, 2016.

(51) Int. Cl.
| | | |
|---|---|---|
| *C10G 65/12* | (2006.01) | |
| *C07C 5/13* | (2006.01) | |
| *C10G 45/14* | (2006.01) | |
| *B01D 3/06* | (2006.01) | |
| *B01D 3/14* | (2006.01) | |

(52) U.S. Cl.
CPC .............. *C10G 65/12* (2013.01); *B01D 3/06* (2013.01); *B01D 3/143* (2013.01); *C07C 5/13* (2013.01); *C10G 45/14* (2013.01); *B01D 3/14* (2013.01)

(58) Field of Classification Search
CPC .......................... C10G 65/12; C10G 2300/4006
See application file for complete search history.

(56) References Cited

U.S. PATENT DOCUMENTS

| | | | |
|---|---|---|---|
| 2,987,466 A * | 6/1961 | Senger | C10G 47/00 208/110 |
| 3,100,006 A | 8/1963 | Sheets et al. | |
| 4,363,718 A | 12/1982 | Klotz | |
| 5,284,573 A | 2/1994 | LaPierre et al. | |
| 6,436,278 B1 * | 8/2002 | Benazzi | C10G 65/043 208/62 |
| 8,394,255 B2 | 3/2013 | McCarthy et al. | |
| 8,617,383 B2 | 12/2013 | Prentice et al. | |
| 8,845,881 B2 | 9/2014 | Simon et al. | |
| 8,992,764 B2 * | 3/2015 | Prentice | C10G 45/64 208/27 |
| 2003/0019788 A1 * | 1/2003 | Benazzi | C10G 65/12 208/57 |
| 2003/0057133 A1 * | 3/2003 | Benazzi | C10G 45/62 208/49 |
| 2004/0256286 A1 | 12/2004 | Miller et al. | |
| 2012/0248008 A1 * | 10/2012 | Dougherty | C10G 45/64 208/59 |

FOREIGN PATENT DOCUMENTS

| | | |
|---|---|---|
| CN | 103773476 A | 5/2014 |
| RU | 2570649 C1 | 12/2015 |

OTHER PUBLICATIONS

Free, The Akzo-Fina CFI [(Cold-Flow Improvement)] process to improve the quality of the diesel pool, Akzo Nobel Catalysts | Fina Research, World International Fuel Quality & Vehicle Technology, 1996.

Zakarian, "All-hydroprocessing route for high-viscosity index lubes", Energy Progress, vol. 7, No. 1, Mar. 1987, pp. 59-64.

* cited by examiner

*Primary Examiner* — Randy Boyer
(74) *Attorney, Agent, or Firm* — Paschall & Maas Law Office, LLC; James C. Paschall

(57) ABSTRACT

A process and apparatus for quenching a hydrocracked stream to prepare it for hydroisomerization. A fractionated hydroisomerized stream is recycled to quench a hot hydrocracked stream prior to hydroisomerization. Sufficient quenching can inactivate the hydroisomerization catalyst bed. The hydroisomerization catalyst bed can be heated back to hydroisomerization temperature and can actively hydroisomerize again.

16 Claims, 3 Drawing Sheets

PROCESS AND APPARATUS FOR HYDROCRACKING AND HYDROISOMERIZING A HYDROCARBON STREAM

CROSS-REFERENCE TO RELATED APPLICATION

This application claims priority from Provisional Application No. 62/357,244 filed Jun. 30, 2016, the contents of which cited application are hereby incorporated by reference in its entirety.

FIELD

The field is the hydroisomerization of hydrocarbon streams, particularly the hydrocracking and hydroisomerization of hydrocarbon streams.

BACKGROUND

Hydroprocessing can include processes which convert hydrocarbons in the presence of hydroprocessing catalyst and hydrogen to more valuable products. Hydrocracking is a hydroprocessing process in which hydrocarbons crack in the presence of hydrogen and hydrocracking catalyst to lower molecular weight hydrocarbons. Depending on the desired output, a hydrocracking unit may contain one or more fixed beds of the same or different catalyst. Hydroisomerization or dewaxing is a hydroprocessing process that increases the alkyl branching on a hydrocarbon backbone in the presence of hydrogen and hydroisomerization catalyst to increase cold flow properties of the hydrocarbon.

Diesel fuel streams must meet cold flow property specifications particularly for winter fuel use. One cold flow property is "pour point" which is the temperature at which a hydrocarbon stream becomes semi-solid and loses its flow characteristics. A high pour point is generally associated with a higher normal paraffin content or a normal paraffin content comprising higher carbon number. Another cold flow property is "cloud point" which is the temperature below which wax in the hydrocarbon stream begins to form a cloudy appearance. The "cold filter plugging point" of diesel fuel is the temperature at which the presence of solidified waxes clogs fuel filters and injectors in engines. The wax also can accumulate on cold surfaces such as on a pipeline or heat exchanger tube and form an emulsion with water.

When hydrocracking gas oil, cold flow property specifications for diesel product can limit the obtainable diesel yield by requiring a lower diesel cut point. Unconverted oil (UCO) is the material boiling above the diesel cut point. A portion of UCO can be recycled in a single-stage or two-stage hydrocracking process configuration as recycle oil or simply recovered as UCO in a once-through hydrocracking process configuration. It is desirable to decrease the product diesel cold flow property temperature values without reducing the diesel cut point to preserve more diesel yield. This can be accomplished by adding a hydroisomerization unit to decrease cold flow property temperature values without decreasing the cut point for the UCO.

There is a continuing need, therefore, for improved methods and apparatuses for hydrocracking and hydroisomerizing hydrocarbon streams.

BRIEF SUMMARY

We have discovered an apparatus and process for hydroisomerizing a hydrocarbon stream after it is hydrocracked. To achieve the desirable hydroisomerization feed temperature, the hydrocracked effluent stream is quenched with a recycle oil stream. If desired, the recycle oil stream can be cooled to such an extent to cool the hydroisomerization catalyst bed to inactivate the hydroisomerization catalyst bed during warmer months.

DEFINITIONS

Figure 1:
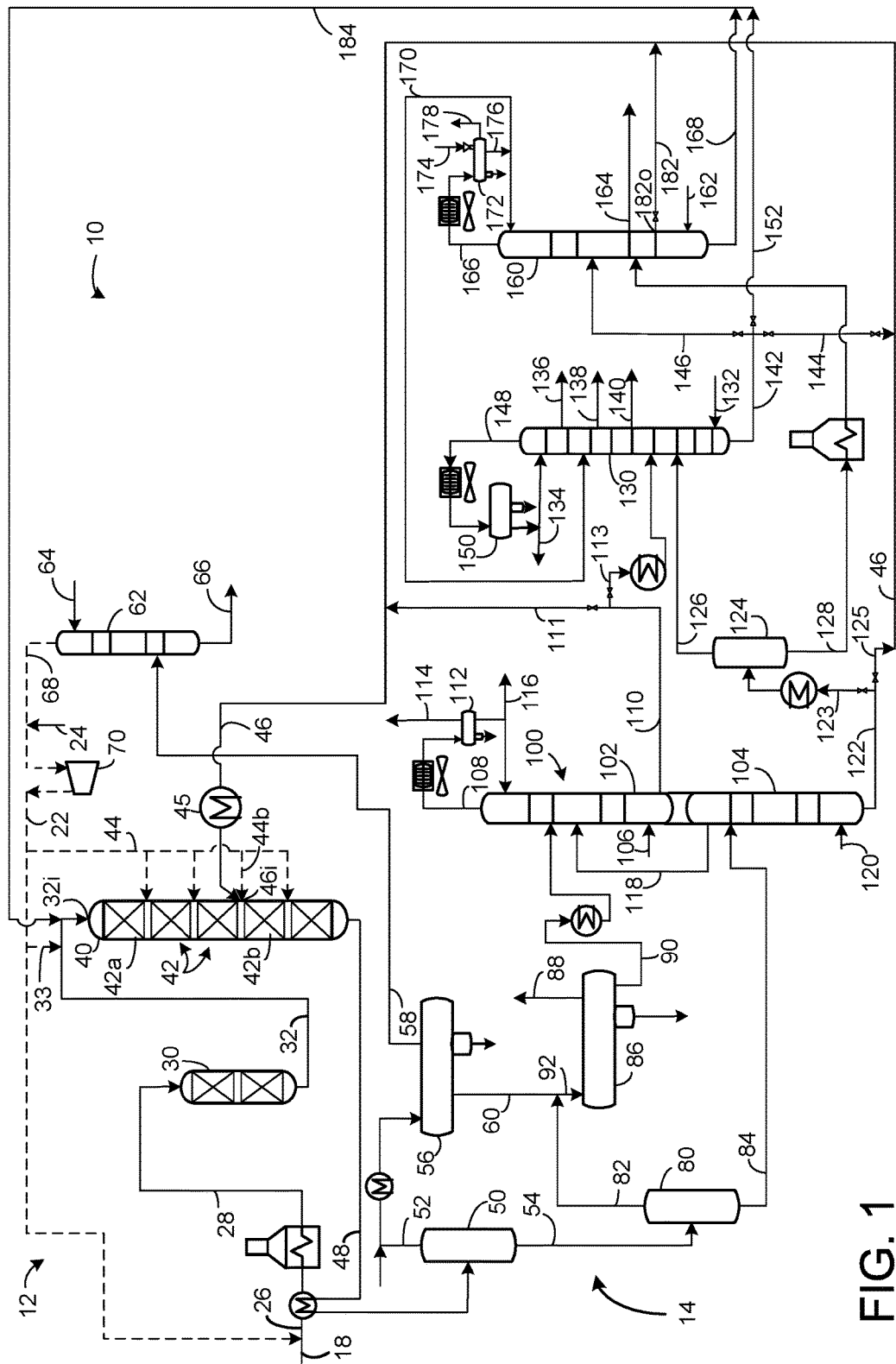
FIG. 1 is a schematic drawing of a hydrocracking unit.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Absorber and scrubbing columns do not include a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise indicated. Stripping columns omit a reboiler at a bottom of the column and instead utilize feed preheat and provide additional heating requirements and separation impetus from a fluidized inert vaporous media such as steam.

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % or liquid volume % distilled is produced using fifteen theoretical plates in a column with a 5:1 reflux ratio.

As used herein, the term "initial boiling point" (IBP) means the temperature at which the sample begins to boil using ASTM D-86.

As used herein, the term "T5" or "T95" means the temperature at which 5 volume percent or 95 volume percent, as the case may be, respectively, of the sample boils using ASTM D-86 or ASTM D-1160.

As used herein, the term "diesel boiling range" means hydrocarbons boiling in the range of between about 132° C. (270° F.) and the diesel cut point between about 343° C. (650° F.) and about 399° C. (750° F.) using the TBP distillation method.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator which latter may be operated at higher pressure.

DETAILED DESCRIPTION

However, hydrotreating reactions that inevitably occur in conjunction with hydrocracking reactions such as the rehydrogenation of hydrocracking reaction intermediates are exothermic which cause the hydrocracked effluent to be higher in temperature than the feed temperature. The hydrocracked effluent is typically at a temperature higher than the optimal feed temperature for the hydroisomerization reaction. Hence, we propose to quench the hydrocracked effluent with recycle oil before it enters the hydroisomerization reaction zone. This will lower the temperature of the hydrocracked effluent and also subject the unconverted recycle oil to a second stage of hydroisomerization reaction.

We have also found that by cooling the recycle oil to a sufficiently low temperature and feeding it to the hydroisomerization reaction zone, the hydroisomerization catalyst can be inactivated. Consequently, the hydroisomerization catalyst bed can be located in the same reactor vessel downstream of a hydrocracking catalyst bed. The hydroisomerization catalyst bed can be turned off during the warmer seasons when cold flow properties are not so stringent to preserve more of the valuable diesel product.

The process and apparatus has been demonstrated in pilot plant studies of being capable of meeting the Arctic Diesel Specifications of a Cloud Point Temperature of −40° C. and Pour Point of −45° C., while providing an increase in distillate yield in the range of 4 to 5 wt % relative to the next best alternative case in which the diesel cut point is reduced to achieve the same cold flow specifications.

The apparatus and process 10 for hydrocracking and hydroisomerizing a hydrocarbon stream comprise a hydroprocessing unit 12 and a fractionation section 14. A hydrocarbonaceous stream in hydrocarbon line 18 and a make-up hydrogen stream hydrogen line 24 are fed to the hydroprocessing unit 12.

In one aspect, the process and apparatus described herein are particularly useful for hydroprocessing a hydrocarbon feed stream comprising a hydrocarbonaceous feedstock. Illustrative hydrocarbonaceous feed stocks include hydrocarbon streams having initial boiling points (IBP) above about 288° C. (550° F.), such as atmospheric gas oils, vacuum gas oil (VGO) having T5 and T95 between about 315° C. (600° F.) and about 600° C. (1100° F.), deasphalted oil, coker distillates, straight run distillates, pyrolysis-derived oils, high boiling synthetic oils, cycle oils, hydrocracked feeds, catalytic cracker distillates, atmospheric residue having an IBP at or above about 343° C. (650° F.) and vacuum residue having an IBP above about 510° C. (950° F.).

A hydrogen stream in hydrogen line 22 is partially provided by the make-up hydrogen stream from line 24. The hydrogen stream may join the hydrocarbonaceous stream in feed line 18 to provide a hydrocarbon feed stream in a hydrocarbon feed line 26. The hydrocarbon feed stream in the hydrocarbon feed line 26 may be heated by heat exchange with a hydroisomerized effluent stream in line 48 and in a fired heater. The heated hydrocarbon feed stream in line 28 may be fed to a hydrotreating reactor 30.

Hydrotreating is a process wherein hydrogen is contacted with hydrocarbon in the presence of hydrotreating catalysts which are primarily active for the removal of heteroatoms, such as sulfur, nitrogen, oxygen and metals from the hydrocarbon feedstock. In hydrotreating, hydrocarbons with double and triple bonds such as olefins may be saturated. Aromatics may also be saturated. Some hydrotreating processes are specifically designed to saturate aromatics.

The hydrotreating reactor 30 may comprise a guard bed of hydrotreating catalyst followed by one or more beds of higher activity hydrotreating catalyst. The guard bed filters particulates and reacts with contaminants in the hydrocarbon feed stream such as metals like nickel, vanadium, silicon and arsenic which are detrimental to the higher activity hydrotreating catalyst. The guard bed may comprise material similar to the hydrotreating catalyst.

Suitable hydrotreating catalysts for use in the present invention are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. More than one type of hydrotreating catalyst may be used in the same hydrotreating reactor 30. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %.

Preferred reaction conditions in the hydrotreating reactor 30 include a temperature from about 290° C. (550° F.) to about 455° C. (850° F.), suitably 316° C. (600° F.) to about 427° C. (800° F.), a pressure from about 2.1 MPa (gauge) (300 psig), preferably 4.1 MPa (gauge) (600 psig) to about 20.6 MPa (gauge) (3000 psig), suitably 12.4 MPa (gauge) (1800 psig), a liquid hourly space velocity of the fresh hydrocarbonaceous feedstock from about 0.1 $hr^{-1}$, suitably 4 $hr^{-1}$, to about 8 $hr^{-1}$, preferably from about 1.5 to about 3.5 $hr^{-1}$, and a hydrogen rate of about 168 $Nm^3/m^3$ (1,000 scf/bbl), to about 1,011 $Nm^3/m^3$ oil (6,000 scf/bbl), preferably about 168 $Nm^3/m^3$ oil (1,000 scf/bbl) to about 674 $Nm^3/m^3$ oil (4,000 scf/bbl), with a hydrotreating catalyst or a combination of hydrotreating catalysts.

The hydrotreating reactor 30 provides a hydrotreated stream that exits the hydrotreating reactor 30 in a hydrotreating effluent line 32. The hydrogen gas laden with ammonia and hydrogen sulfide may be removed from the hydrotreated hydrocarbon stream in a separator, but the hydrotreated hydrocarbon stream is typically fed directly to the hydrocracking reactor 40 without separation. The hydrotreated hydrocarbon feed stream may be mixed with a hydrocracking hydrogen stream in a hydrocracking hydrogen line 33 from the hydrogen line 22 and optionally a recycle oil stream from a second recycle oil line 184 and is fed through a first inlet 32*i* to the hydrocracking reactor 40 to be hydrocracked.

Hydrocracking refers to a process in which hydrocarbons crack in the presence of hydrogen to lower molecular weight hydrocarbons. The hydrocracking reactor 40 may be a fixed bed reactor that comprises one or more vessels, single or multiple catalyst beds 42 in each vessel, and various combinations of hydrotreating catalyst, hydroisomerization catalyst and/or hydrocracking catalyst in one or more vessels. It is contemplated that the hydrocracking reactor 40 be operated in a continuous liquid phase in which the volume of the liquid hydrocarbon feed is greater than the volume of the hydrogen gas. The hydrocracking reactor 40 may also be operated in a conventional continuous gas phase, a moving bed or a fluidized bed hydroprocessing reactor.

The hydrocracking reactor may provide a total conversion of at least about 20 vol % and typically greater than about 60 vol % of the hydrocarbon feed to products boiling below the diesel cut point. A hydrocracking reactor may operate at partial conversion of more than about 30 vol % or full conversion of at least about 90 vol % of the feed based on total conversion. A hydrocracking reactor may be operated at mild hydrocracking conditions which will provide about 20 to about 60 vol %, preferably about 20 to about 50 vol %, total conversion of the hydrocarbon feed stream to product boiling below the diesel-cut point. The diesel cut point can be selected to maximize the production of diesel.

The hydrocracking reactor 40 comprises a plurality of catalyst beds 42. If the hydroprocessing unit 12 does not include a hydrotreating reactor 30, the first bed in the hydrocracking reactor 40 may include hydrotreating catalyst for the purpose of saturating, demetallizing, desulfurizing, deoxygenating or denitrogenating the hydrocarbon feed before it is hydrocracked with hydrocracking catalyst in subsequent vessels or catalyst beds 42 in the hydrocracking reactor 40. Otherwise, the first or an upstream bed in the hydrocracking reactor 40 may comprise a first hydrocracking catalyst bed 42*a*.

A hydrocracking catalyst may utilize amorphous silica-alumina bases or low-level zeolite bases combined with one or more Group VIII or Group VIB metal hydrogenating components if mild hydrocracking is desired to produce a balance of middle distillate and gasoline. In another aspect, when middle distillate is significantly preferred in the converted product over gasoline production, partial or full hydrocracking may be performed in the first hydrocracking reactor 40 with a catalyst which comprises, in general, any crystalline zeolite cracking base upon which is deposited a Group VIII metal hydrogenating component. Additional hydrogenating components may be selected from Group VIB for incorporation with the zeolite base.

The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and about 14 Angstroms ($10^{-10}$ meters). It is preferred to employ zeolites having a relatively high silica/alumina mole ratio between about 3 and about 12. Suitable zeolites found in nature include, for example, mordenite, stilbite, heulandite, ferrierite, dachiardite, chabazite, erionite and faujasite. Suitable synthetic zeolites include, for example, the B, X, Y and L crystal types, e.g., synthetic faujasite and mordenite. The preferred zeolites are those having crystal pore diameters between about 8 and 12 Angstroms ($10^{-10}$ meters), wherein the silica/alumina mole ratio is about 4 to 6. One example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,100,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. In one aspect, the preferred cracking bases are those which are at least about 10 wt %, and preferably at least about 20 wt %, metal-cation-deficient, based on the initial ion-exchange capacity. In another aspect, a desirable and stable class of zeolites is one wherein at least about 20 wt % of the ion exchange capacity is satisfied by hydrogen ions.

The active metals employed in the preferred hydrocracking catalysts of the present invention as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 wt % and about 30 wt % may be used. In the case of the noble metals, it is normally preferred to use about 0.05 to about 2 wt % noble metal.

The method for incorporating the hydrogenation metal is to contact the base material with an aqueous solution of a suitable compound of the desired metal wherein the metal is present in a cationic form. Following addition of the selected hydrogenation metal or metals, the resulting catalyst powder is then filtered, dried, pelleted with added lubricants, binders or the like if desired, and calcined in air at temperatures of, e.g., about 371° C. (700° F.) to about 648° C. (1200° F.) in order to activate the catalyst and decompose ammonium ions. Alternatively, the base component may first be pelleted, followed by the addition of the hydrogenation component and activation by calcining.

The foregoing catalysts may be employed in undiluted form, or the powdered catalyst may be mixed and co-pelleted with other relatively less active catalysts, diluents or binders such as alumina, silica gel, silica-alumina co-gels, activated clays and the like in proportions ranging between about 5 and about 90 wt %. These diluents may be employed as such or they may contain a minor proportion of an added hydrogenating metal such as a Group VIB and/or Group VIII metal. Additional metal promoted hydrocracking catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718.

By one approach, the hydrocracking conditions may include a temperature from about 290° C. (550° F.) to about 468° C. (875° F.), preferably 343° C. (650° F.) to about 445°

C. (833° F.), a pressure from about 4.8 MPa (gauge) (700 psig) to about 20.7 MPa (gauge) (3000 psig), a liquid hourly space velocity (LHSV) from about 0.4 to less than about 2.5 hr$^{-1}$ and a hydrogen rate of about 421 Nm$^3$/m$^3$ (2,500 scf/bbl) to about 2,527 Nm$^3$/m$^3$ oil (15,000 scf/bbl). If mild hydrocracking is desired, conditions may include a temperature from about 315° C. (600° F.) to about 441° C. (825° F.), a pressure from about 5.5 MPa (gauge) (800 psig) to about 13.8 MPa (gauge) (2000 psig) or more typically about 6.9 MPa (gauge) (1000 psig) to about 11.0 MPa (gauge) (1600 psig), a liquid hourly space velocity (LHSV) from about 0.5 to about 2 hr$^{-1}$ and preferably about 0.7 to about 1.5 hr$^{-1}$ and a hydrogen rate of about 421 Nm$^3$/m$^3$ oil (2,500 scf/bbl) to about 1,685 Nm$^3$/m$^3$ oil (10,000 scf/bbl).

The hydrotreated hydrocarbon feed stream is hydrocracked over the first hydrocracking catalyst bed 42a in the presence of a hydrogen stream to provide a hydrocracked stream. Subsequent catalyst beds 42 in the hydrocracking reactor may comprise hydrocracking catalyst over which additional hydrocracking occurs to the hydrocracked stream. Hydrogen manifold 44 may deliver supplemental hydrogen streams to one, some or each of the catalyst beds 42. In an aspect, the supplemental hydrogen is added to each of the catalyst beds 42 at an interstage location between adjacent beds, so supplemental hydrogen is mixed with hydroprocessed effluent exiting from the upstream catalyst bed 42 before entering the downstream catalyst bed 42.

At least one downstream catalyst bed may comprise a first hydroisomerization catalyst bed 42b. The hydrocracked stream is hydroisomerized over a first hydroisomerization catalyst bed in the presence of a supplemental hydrogen stream from a manifold branch line 44b to provide a hydroisomerized stream. The first hydrocracking catalyst bed 42a and the first hydroisomerization catalyst bed 42b may be located in the first hydrocracking reactor 40. Additional hydrocracking catalyst beds 42 may be located between the first hydrocracking catalyst bed 42a and the first hydroisomerization catalyst bed 42b.

The hydroisomerization catalyst can comprise an unbound 10-member ring pore, one-dimensional zeolite in combination with a low surface area metal oxide refractory binder, both of which are selected to obtain a high ratio of micropore surface area to total surface area. Alternatively, the zeolite has a low silica to alumina ratio. Suitable catalysts include 10-member ring pore zeolites, such as EU-1, ZSM-35 (or ferrierite), ZSM-11, ZSM-57, NU-87, SAPO-11, and ZSM-22. Preferred materials are EU-2, EU-11, ZBM-30, ZSM-48, or ZSM-23. ZSM-48 is most preferred. Note that a zeolite having the ZSM-23 structure with a silica to alumina ratio of from about 20:1 to about 40:1 can sometimes be referred to as SSZ-32. Other molecular sieves that are isostructural with the above materials include Theta-1, NU-10, EU-13, KZ-1, and NU-23.

The hydroisomerization catalyst can further include a metal hydrogenation function, such as a Group VI or Group VIII metal, and suitably a Group VIII noble metal. The metal hydrogenation component is typically a Group VI and/or a Group VIII metal. The metal hydrogenation component may be a Group VIII noble metal. Preferably, the metal hydrogenation component is a combination of a non-noble Group VIII metal with a Group VI metal. Suitable combinations can include nickel, cobalt, or iron with molybdenum or tungsten, preferably nickel with molybdenum or tungsten.

The metal hydrogenation component may be added to the catalyst in any convenient manner. One technique for adding the metal hydrogenation component is by incipient wetness. For example, after combining a zeolite and a binder, the combined zeolite and binder can be extruded into catalyst particles. These catalyst particles can then be exposed to a solution containing a suitable metal precursor. Alternatively, metal can be added to the catalyst by ion exchange, where a metal precursor is added to a mixture of zeolite (or zeolite and binder) prior to extrusion.

The amount of metal in the catalyst can be at least about 0.1 wt % to about 10 wt % based on catalyst. Preferably, the hydroisomerization catalysts have a low ratio of silica to alumina. In various embodiments, the ratio of silica to alumina can be from 30:1 to 200:1, 60:1 to 110:1, or 70:1 to 100:1. The hydroisomerization catalysts may also include an optional binder having a low surface area such as 100 m$^2$/g or less, or 80 m$^2$/g or less, or 70 m$^2$/g or less. A zeolite can be combined with binder by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture. The amount of framework alumina in the catalyst may range from 0.1 to 3.33 wt %, or 0.1 to 2.7 wt %, or 0.2 to 2 wt %, or 0.3 to 1 wt %.

The hydroisomerization catalyst maintains catalytic activity even if substantial sulfur is present in the hydrocracked stream such as when hydrogen sulfide gas is not removed from the hydrogen stream following hydrotreating or hydrocracking. The hydrocracked stream may contain up to about 4.0 wt % at least about 0.1 wt % of sulfur and be effectively hydroisomerized. Sulfur content may be measured by standard ASTM methods D2622.

Process conditions in the hydroisomerization catalyst bed may include a temperature of from 200 to 450° C., preferably 270 to 400° C., a hydrogen partial pressure of from 1.8 mPa (250 psi) to 34.6 mPa (5000 psi), preferably 4.8 mPa (667 psi) to 20.8 mPa (3005 psi), a liquid hourly space velocity of from 0.2 to 10 v/v/hr, preferably 4 to 8 v/v/hr, and a hydrogen circulation rate of from 35.6 Nm$^3$/m$^3$ (200 scf/B), to 1781 Nm$^3$/m$^3$ (10,000 scf/B), preferably 890 Nm$^3$/m$^3$ (5000 scf/B) to 1424 Nm$^3$/m$^3$ (8000 scf/B). The hydroisomerization process is conducted at a lower temperature than the hydrocracking process and at a lower temperature than the temperature of the effluent from the first hydrocracking catalyst bed 42a or other downstream hydrocracking catalyst bed(s) 42 comprising the hydrocracked stream. Accordingly, a first fractionated stream is recycled to the first isomerization catalyst bed 42b to quench the hydrocracked stream entering the first hydroisomerization catalyst bed 42b from the superjacent catalyst bed 42. The first fractionated stream in line 46 may be cooled in a heat exchanger 45 before entering the first isomerization catalyst bed 42b. The first fractionated stream in line 46 may be fed to the first hydrocracking reactor 40 through an intermediate inlet 46i which is downstream of the first inlet 32i to the first hydrocracking catalyst bed 42a. The first fractionated stream may be fed from line 46 to the intermediate inlet 46i after receiving a supplement hydrogen stream from the manifold branch 44b from the hydrogen manifold 44 to the first isomerization catalyst bed 42b. The first fractionated stream reduces the overall temperature of the combined stream comprising the hydrocracked stream, the supplemental hydrogen stream and the first fractionated stream entering the first hydroisomerization catalyst bed to a desired hydroisomerization reaction temperature.

The addition of the second fractionated stream to the first catalyst bed 42b increases the residence time of the hydrocracked product on the hydroisomerization catalyst and increases the space velocity on all the downstream catalyst beds 42 to about 6 to about 10 hr$^{-1}$. The catalyst volume can be increased to hold the space velocity to typical value of about 5 to about 8 hr$^{-1}$ if desired.

In summer months, when cold flow specifications are not as stringent, the first hydroisomerization catalyst bed 42b can be inactivated by cooling the first fractionated stream in line 46 sufficiently, so the temperature of the combined stream entering the first hydrocracking catalyst bed 42b has an inactivation temperature between about 274° C. (525° F.) and about 302° C. (575° F.) or about 307° C. (585° F.), preferably less than about 288° C. (550° F.) and certainly less than about 260° C. (500° F.). We have found at these temperatures, the hydroisomerization catalyst is inactive, such that it does not chemically alter the composition of the hydrocracked stream entering the first hydroisomerization catalyst bed. We have also found that the hydroisomerization catalyst can be reactivated by heating the combined stream entering the first hydroisomerization catalyst bed 42b to above the inactivation temperature. The reactivated hydroisomerization catalyst bed 42b has a hydroisomerization catalyst activity substantially the same as it was before it was inactivated. Partial inactivation of the hydroisomerization catalyst bed can be achieved by reducing the temperature of the combined stream sufficiently to reduce the temperature of the first hydroisomerization catalyst bed 42b to 22° C. (40° F.) below hydroisomerization reaction temperature which can fluctuate depending on the activity of the hydrocracking catalyst, space velocity, etc.

The hydroisomerized stream from the first hydroisomerization catalyst bed 42b may enter into a subsequent hydrocracking catalyst bed(s) 42 to be hydrocracked over hydrocracking catalyst over a supplemental hydrogen stream from the hydrogen manifold 44 and/or enter into a subsequent hydroisomerization catalyst bed(s) 42 to be hydroisomerized over hydroisomerization catalyst over a supplemental hydrogen stream from the hydrogen manifold 44 or be taken directly to the fractionation section 14. Even if this stream from the first hydroisomerization catalyst bed 42b is subsequently hydrocracked, it is still considered a hydroisomerized stream.

The hydroisomerized stream may be separated in the fractionation section 14 in downstream communication with the hydrocracking reactor 40. The fractionation section 14 comprises one or more separators and fractionation columns in downstream communication with the hydrocracking reactor 40.

The hydroisomerized stream in hydroisomerized line 48 may in an aspect be heat exchanged with the hydrocarbon feed stream in line 26 to be cooled before entering a hot separator 50. The hot separator separates the hydroprocessed effluent stream to provide a hydrocarbonaceous, hot gaseous stream in a hot overhead line 52 and a hydrocarbonaceous, hot liquid stream in a hot bottoms line 54. The hot separator 50 may be in downstream communication with the hydrocracking reactor 40. The hot separator 50 operates at about 177° C. (350° F.) to about 371° C. (700° F.) and preferably operates at about 232° C. (450° F.) to about 315° C. (600° F.). The hot separator 50 may be operated at a slightly lower pressure than the hydrocracking reactor 40 accounting for pressure drop through intervening equipment. The hot separator 50 may be operated at pressures between about 3.4 MPa (gauge) (493 psig) and about 20.4 MPa (gauge) (2959 psig). The hydrocarbonaceous, hot gaseous separated stream in the hot overhead line 52 may have a temperature of the operating temperature of the hot separator 50.

The hot gaseous stream in the hot overhead line 52 may be cooled before entering a cold separator 56. As a consequence of the reactions taking place in the hydrocracking reactor 40 wherein nitrogen, chlorine and sulfur are removed from the feed, ammonia and hydrogen sulfide are formed. At a characteristic sublimation temperature, ammonia and hydrogen sulfide will combine to form ammonium bisulfide and ammonia, and chlorine will combine to form ammonium chloride. Each compound has a characteristic sublimation temperature that may allow the compound to coat equipment, particularly heat exchange equipment, impairing its performance. To prevent such deposition of ammonium bisulfide or ammonium chloride salts in the hot overhead line 36 transporting the hot gaseous stream, a suitable amount of wash water may be introduced into the hot overhead line 52 upstream of a cooler at a point in the hot overhead line where the temperature is above the characteristic sublimation temperature of either compound.

The hot gaseous stream may be separated in the cold separator 56 to provide a cold gaseous stream comprising a hydrogen-rich gas stream in a cold overhead line 58 and a cold liquid stream in a cold bottoms line 60. The cold separator 56 serves to separate hydrogen rich gas from hydrocarbon liquid in the hydroisomerized stream for recycle to the hydrocracking reactor 40 in the cold overhead line 58. The cold separator 56, therefore, is in downstream communication with the hot overhead line 52 of the hot separator 50 and the hydrocracking reactor 40. The cold separator 56 may be operated at about 100° F. (38° C.) to about 150° F. (66° C.), suitably about 115° F. (46° C.) to about 145° F. (63° C.), and just below the pressure of the hydrocracking reactor 40 and the hot separator 50 accounting for pressure drop through intervening equipment to keep hydrogen and light gases in the overhead and normally liquid hydrocarbons in the bottoms. The cold separator 56 may be operated at pressures between about 3 MPa (gauge) (435 psig) and about 20 MPa (gauge) (2,901 psig). The cold separator 56 may also have a boot for collecting an aqueous phase. The cold liquid stream in the cold bottoms line 60 may have a temperature of the operating temperature of the cold separator 56.

The cold gaseous stream in the cold overhead line 58 is rich in hydrogen. Thus, hydrogen can be recovered from the cold gaseous stream. The cold gaseous stream in the cold overhead line 58 may be passed through a trayed or packed recycle scrubbing column 62 where it is scrubbed by means of a scrubbing extraction liquid such as an aqueous solution fed by line 64 to remove acid gases including hydrogen sulfide and carbon dioxide by extracting them into the aqueous solution. Preferred aqueous solutions include lean amines such as alkanolamines DEA, MEA, and MDEA. Other amines can be used in place of or in addition to the preferred amines. The lean amine contacts the cold gaseous stream and absorbs acid gas contaminants such as hydrogen sulfide and carbon dioxide. The resultant "sweetened" cold gaseous stream is taken out from an overhead outlet of the recycle scrubber column 62 in a recycle scrubber overhead line 68, and a rich amine is taken out from the bottoms at a bottom outlet of the recycle scrubber column in a recycle scrubber bottoms line 66. The spent scrubbing liquid from the bottoms may be regenerated and recycled back to the recycle scrubbing column 62 in line 64. The scrubbed hydrogen-rich stream emerges from the scrubber via the recycle scrubber overhead line 68 and may be compressed in a recycle compressor 70 to provide the hydrogen stream in the hydrogen line 22 and a supplemental hydrogen stream in a supplemental hydrogen manifold 44. The scrubbed hydrogen-rich stream in the scrubber overhead line 68 may be supplemented with make-up hydrogen stream in the make-up line 24 upstream or downstream of the compressor 70. The recycle hydrogen manifold 44 feeds portions of the recycle hydrogen stream to catalyst beds 42 in the hydrocracking reactor 40 to control the inlet temperature of the downstream catalyst beds. The recycle scrubbing column 62 may be operated with a gas inlet temperature between about 38° C. (100° F.) and about 66° C. (150° F.) and an overhead pressure of about 3 MPa (gauge) (435 psig) to about 20 MPa (gauge) (2900 psig).

The hydrocarbonaceous hot liquid stream in the hot bottoms line 60 may be fractionated. In an aspect, the hot liquid stream in the hot bottoms line 54 may be let down in pressure and flashed in a hot flash drum 80 to provide a flash hot gaseous stream of light ends in a flash hot overhead line 82 and a flash hot liquid stream in a flash hot bottoms line 84. The hot flash drum 80 may be in direct, downstream communication with the hot bottoms line 54 and in downstream communication with the hydrocracking reactor 40. In an aspect, light gases such as hydrogen sulfide may be stripped from the flash hot liquid stream in the flash hot bottoms line 84. Accordingly, a stripping column 100 may be in downstream communication with the hot flash drum 80 and the hot flash bottoms line 84.

The hot flash drum 80 may be operated at the same temperature as the hot separator 50 but at a lower pressure of between about 1.4 MPa (gauge) (200 psig) and about 6.9 MPa (gauge) (1000 psig), suitably no more than about 3.8 MPa (gauge) (550 psig). The flash hot liquid stream in the flash hot bottoms line 84 may be further fractionated in the fractionation section 14. The flash hot liquid stream in the flash hot bottoms line 84 may have a temperature of the operating temperature of the hot flash drum 80.

In an aspect, the cold liquid stream in the cold bottoms line 60 may be directly fractionated. In a further aspect, the cold liquid stream may be let down in pressure and flashed in a cold flash drum 86 to separate the cold liquid stream in the cold bottoms line 60. The cold flash drum 86 may be in direct downstream communication with the cold bottoms line 60 of the cold separator 56 and in downstream communication with the hydrocracking reactor 40.

In a further aspect, the flash hot gaseous stream in the flash hot overhead line 82 may be fractionated in the fractionation section 14. In a further aspect, the flash hot gaseous stream may be cooled and also separated in the cold flash drum 86. The cold flash drum 86 may separate the cold liquid stream in line 60 and/or the flash hot gaseous stream in the flash hot overhead line 82 to provide a flash cold gaseous stream in a flash cold overhead line 88 and a flash cold liquid stream in a cold flash bottoms line 90. In an aspect, light gases such as hydrogen sulfide may be stripped from the flash cold liquid stream in the flash cold bottoms line 90. Accordingly, a stripping column 100 may be in downstream communication with the cold flash drum 86 and the cold flash bottoms line 90.

The cold flash drum 86 may be in downstream communication with the cold bottoms line 60 of the cold separator 56, the hot flash overhead line 82 of the hot flash drum 80 and the hydrocracking reactor 40. The flash cold liquid stream in the cold bottoms line 60 and the flash hot gaseous stream in the hot flash overhead line 82 may enter into the cold flash drum 86 either together or separately. In an aspect, the hot flash overhead line 82 joins the cold bottoms line 60 and feeds the flash hot gaseous stream and the cold liquid stream together to the cold flash drum 86 in a cold flash feed line 92. The cold flash drum 86 may be operated at the same temperature as the cold separator 56 but typically at a lower pressure of between about 1.4 MPa (gauge) (200 psig) and about 6.9 MPa (gauge) (1000 psig) and preferably between about 3.0 MPa (gauge) (435 psig) and about 3.8 MPa (gauge) (550 psig). A flashed aqueous stream may be removed from a boot in the cold flash drum 86. The flash cold liquid stream in the flash cold bottoms line 90 may have the same temperature as the operating temperature of the cold flash drum 86. The flash cold gaseous stream in the flash cold overhead line 88 contains substantial hydrogen that may be recovered.

The fractionation section 14 may further include the stripping column 100, a atmospheric fractionation column 130 and a vacuum fractionation column 160. The stripping column 100 may be in downstream communication with a bottoms line in the fractionation section 14 for stripping volatiles from a hydroisomerized stream. For example, the stripping column 100 may be in downstream communication with the hot bottoms line 54, the flash hot bottoms line 84, the cold bottoms line 60 and/or the cold flash bottoms line 90. In an aspect, the stripping column 100 may be a vessel that contains a cold stripping column 102 and a hot stripping column 104 with a wall that isolates each of the stripping columns 102, 104 from the other. The cold stripping column 102 may be in downstream communication with the hydrocracking reactor 40, the cold bottoms line 60 and, in an aspect, the flash cold bottoms line 90 for stripping the cold liquid stream. The hot stripping column 104 may be in downstream communication with the hydrocracking reactor 40 and the hot bottoms line 54 and, in an aspect, the flash hot bottoms line 84 for stripping a hot liquid stream which is hotter than the cold liquid stream. The hot liquid stream may be hotter than the cold liquid stream, by at least 25° C. and preferably at least 50° C.

The flash cold liquid stream comprising a hydroisomerized stream in the flash cold bottoms line 90 may be heated and fed to the cold stripping column 102 at an inlet which may be in a top half of the column. The flash cold liquid stream which comprises a hydroisomerized stream may be stripped of gases in the cold stripping column 102 with a cold stripping media which is an inert gas such as steam from a cold stripping media line 106 to provide a cold stripper gaseous stream of naphtha, hydrogen, hydrogen sulfide, steam and other gases in a cold stripper overhead line 108 and a cold stripped stream in a cold stripper bottoms line 110. The cold stripper gaseous stream in the cold stripper overhead line 108 may be condensed and separated in a receiver 112. A stripper net overhead line 114 from the receiver 112 carries a net stripper gaseous stream for further recovery of LPG and hydrogen in a light material recovery unit. Unstabilized liquid naphtha from the bottoms of the receiver 112 may be split between a reflux portion refluxed to the top of the cold stripping column 102 and a liquid stripper overhead stream which may be transported in a condensed stripper overhead line 116 to further recovery or processing. A sour water stream may be collected from a boot of the overhead receiver 112.

The cold stripping column 102 may be operated with a bottoms temperature between about 149° C. (300° F.) and about 288° C. (550° F.), preferably no more than about 260° C. (500° F.), and an overhead pressure of about 0.35 MPa (gauge) (50 psig), preferably no less than about 0.70 MPa (gauge) (100 psig), to no more than about 2.0 MPa (gauge) (290 psig). The temperature in the overhead receiver 112 ranges from about 38° C. (100° F.) to about 66° C. (150° F.) and the pressure is essentially the same as in the overhead of the cold stripping column 102.

The cold stripped stream in the cold stripper bottoms line 110 may comprise predominantly naphtha and kerosene boiling materials. A portion or all of the cold stripped stream in line 110 may be recycled in a cold stripper transfer line 111 to the first isomerization catalyst bed 42b as a first fractionated stream in the first recycle line 46. A remaining portion or all of the cold stripped stream in the cold fractionator feed line 113 comprising a hydroisomerized stream from the cold stripper bottoms line 110 may be heated and fed to the atmospheric fractionation column 130. The atmospheric fractionation column 130 may be in downstream communication with the cold stripper bottoms line 110 of the cold stripping column 102 and the stripping column 100. In an aspect, the atmospheric fractionation column 130 may comprise more than one fractionation column. The atmospheric fractionation column 130 may be in downstream communication with one, some or all of the hot separator 50, the cold separator 56, the hot flash drum 80 and the cold flash drum 86.

The flash hot liquid stream comprising a hydroisomerized stream in the hot flash bottoms line 90 may be fed to the hot stripping column 104 near a top thereof. The flash hot liquid stream may be stripped in the hot stripping column 104 of gases with a hot stripping media which is an inert gas such as steam from a line 120 to provide a hot stripper overhead stream of naphtha, hydrogen, hydrogen sulfide, steam and other gases in a hot stripper overhead line 118 and a hot stripped stream in a hot stripper bottoms line 122. The hot stripper overhead line 118 may be condensed and a portion refluxed to the hot stripping column 104. However, in the embodiment of FIG. 1, the hot stripper overhead stream in the hot stripper overhead line 118 from the overhead of the hot stripping column 104 may be fed into the cold stripping column 102 directly in an aspect without first condensing or refluxing. The inlet for the cold flash bottoms line 90 carrying the flash cold liquid stream may be at a higher elevation than the inlet for the hot stripper overhead line 118. The hot stripping column 104 may be operated with a bottoms temperature between about 160° C. (320° F.) and about 360° C. (680° F.) and an overhead pressure of about 0.35 MPa (gauge) (50 psig), preferably about 0.70 MPa (gauge) (100 psig), to about 2.0 MPa (gauge) (292 psig).

At least a portion of the hot stripped stream comprising a hydroisomerized stream in the hot stripped bottoms line 122 may be taken in a hot fractionator feed line 123, heated and fed to the atmospheric fractionation column 130. Another portion of the hot stripped stream in the hot stripped bottoms line 122 may be transferred in a hot transfer line 125 to the first recycle line 46 for recycle as a first fractionated stream to the first isomerization catalyst bed 42b. The atmospheric fractionation column 130 may be in downstream communication with the hot stripped bottoms line 122 of the hot stripping column 104. The hot stripped stream in line 122 may be at a hotter temperature than the cold stripped stream in line 110.

In an aspect, the hot stripped stream in the hot fractionator feed line 123 may be heated and fed to a prefractionation separator 124 for separation into a vaporized hot stripped stream in a prefractionation overhead line 126 and a liquid hot stripped stream in a prefractionation bottoms line 128 which both comprise hydroisomerized streams. The vaporous hot stripped stream may be fed to the atmospheric fractionation column 130 in the prefractionation overhead line 128 The liquid hot stripped stream may be heated in a fractionation furnace and fed to the atmospheric fractionation column 130 in the prefractionation bottoms line 128 at an elevation below the elevation at which the prefractionation overhead line 126 feeds the vaporized hot stripped stream to the atmospheric fractionation column 130. In the embodiment illustrated, the liquid hot stripped stream in the prefractionation bottoms line 128 may be heated in a fractionation furnace and fed to an optional vacuum fractionation column 160.

The atmospheric fractionation column 130 may be in downstream communication with the cold stripping column 102 and the hot stripping column 104 and may comprise more than one fractionation column for separating stripped hydroisomerized streams into product streams. The atmospheric fractionation column 130 may fractionate hydroisomerized streams, the cold stripped stream, the vaporous hot stripped stream and the liquid hot stripped stream, with an inert stripping media stream such as steam from line 132 to provide several product streams. The product streams from the atmospheric fractionation column 130 may include a net fractionated overhead stream comprising naphtha in a net overhead line 134, an optional heavy naphtha stream in line 136 from a side cut outlet, a kerosene stream carried in line 138 from a side cut outlet and a diesel stream in line 140 from a side cut outlet.

An atmospheric unconverted oil stream may be provided in an atmospheric bottoms line 142. A portion or all of the atmospheric unconverted oil stream in the atmospheric bottoms line 142 may be transferred in atmospheric transfer line 144 to the first recycle line 46 for recycle to the first hydroisomerization catalyst bed 42b as the first fractionation stream. Alternatively, the portion, some or all of the atmospheric unconverted oil stream in the atmospheric bottoms line 142 may be transferred in an atmospheric transfer line 152 to the hydrocracking reactor 40 in a second recycle line 184 as the second fractionation stream particularly in an embodiment which omits a vacuum fractionation column 160. The remaining portion, if there is one, may be fed to an optional vacuum fractionation column 160 in a vacuum fractionation feed line 146.

Heat may be removed from the atmospheric fractionation column 130 by cooling at least a portion of the product streams and sending a portion of each cooled stream back to the fractionation column. These product streams may also be stripped to remove light materials to meet product purity requirements. A fractionated overhead stream in an overhead line 148 may be condensed and separated in a receiver 150 with a portion of the condensed liquid being refluxed back to the fractionation column 130. The net fractionated overhead stream in line 134 may be further processed or recovered as naphtha product. The atmospheric fractionation column 130 may be operated with a bottoms temperature between about 260° C. (500° F.), and about 385° C. (725° F.), preferably at no more than about 350° C. (650° F.), and at an overhead pressure between about 7 kPa (gauge) (1 psig) and about 69 kPa (gauge) (10 psig). A portion of the unconverted oil stream in the atmospheric bottoms line 142 may be reboiled and returned to the atmospheric fractionation column 130 instead of adding an inert stripping media stream such as steam in line 132 to heat to the atmospheric fractionation column 130.

The liquid hot stripped stream in the prefractionation bottoms line 128 or the hot fractionator feed line 123 may be heated in a fired heater and fed to a vacuum fractionation column 160. In the vacuum fractionation column 160, the liquid hot stripped stream may be fractionated to separate diesel from unconverted oil. The atmospheric unconverted oil stream in the vacuum fractionator feed line 146 may also be fed to the vacuum fractionation column 160 at an inlet above the inlet for the liquid hot stripped stream. In the vacuum fractionation column 160, the unconverted oil stream in the vacuum fractionator feed line 146 may also be fractionated to separate diesel from unconverted oil. The vacuum fractionation column 160 is therefore in downstream communication with the cold stripping column 60, but the atmospheric fractionation column 130 may be in downstream communication with the cold stripping column 102 upstream of the vacuum fractionation column 160. Consequently, the atmospheric fractionation column 130 is in upstream communication with the vacuum fractionation column 160.

An inert gas such as steam from vacuum media line 162 may provide heat to the vacuum fractionation column 160 to help fractionate lighter components from heavier components. The vacuum fractionation column 160 produces a diesel product stream in line 164 from a side cut outlet. Heat may be removed from the vacuum fractionation column 160 by cooling the diesel stream in line 164 and sending a portion of the cooled stream back to the column. The diesel stream in line 164 may also be stripped to remove light materials to meet product purity requirements. The vacuum fractionation column operates to produce a diesel stream with a diesel TBP cut point of between about 370° and about 390° C. and a T95 of no more than 380° C. and preferably no more than 360° C. The diesel stream also meets the Arctic Diesel Specifications of a Cloud Point Temperature of −40° C. and a Pour Point of −45° C. A vacuum fractionated stream in a vacuum transfer line 182 may be taken as a side cut from a side outlet 182o to be recycled to the first isomerization catalyst bed 42b as the first fractionation stream in line 46.

A heavy return stream may be provided from an upper half of the vacuum fractionation column from an overhead outlet in overhead line 166 and/or a side line from a side cut outlet (not shown) and fed in a heavy return line 170 to the atmospheric fractionation column 130. The inlet for the heavy return stream in line 170 in downstream communication with the heavy return line 170 may be at a higher elevation than the inlet for the cold stripped stream in the cold fractionator line 113 or the feed inlet for the vaporous hot stripped stream from the prefractionation overhead line 126 to the atmospheric fractionation column 130. A vacuum unconverted oil stream in a vacuum bottoms line 168 may be recovered from a bottom of the vacuum fractionation column 160. The vacuum unconverted oil stream has a boiling point above the diesel cut point and may be recycled to the hydrocracking reactor 40 or to a second hydrocracking reactor as a second fractionation stream in a second recycle line 184. Additionally, a heavy polynuclear aromatic stream concentrated in heavy polynuclear aromatics may be recovered from the unconverted oil stream in the vacuum bottoms line 168 before the unconverted oil stream is recycled in the second recycle line.

The vacuum fractionation column 160 is operated at below atmospheric pressure in the overhead. The overhead stream in overhead line 166 may feed a vacuum generating device 172. The vacuum generating device 172 may include and eductor in communication with an inert gas stream 174 such as steam which pulls a vacuum on the overhead stream in the overhead line 166. A condensed hydrocarbon stream in line 176 from the vacuum generating device 172 may supply the heavy return stream 170 by itself or with another upper stream from a side line (not shown). A condensed aqueous stream may also be removed from a boot in the vacuum generating device. A hydrocarbonaceous vaporous stream may be removed from the vapor generating device in line 178.

The vacuum fractionation column 160 may be operated with a bottoms temperature between about 260° C. (500° F.), and about 370° C. (700° F.), preferably about 300° C. (570° F.), and at an overhead pressure between about 10 kPa (absolute) (1.5 psia), preferably about 20 kPa (absolute) (3 psia), and about 70 kPa (gauge) (10 psig). A portion of the unconverted oil in the vacuum bottoms line 168 may be reboiled and returned to the vacuum fractionation column 160 instead of using steam stripping to add heat to the vacuum fractionation column 160.

The first fractionation stream in the first recycle line 46 may be cooled in the heat exchanger 45 and fed to the first hydroisomerization catalyst bed 42b in the first hydrocracking reactor 40 to be further hydroisomerized in the presence of a supplemental hydrogen stream from branch line 44b. The first fractionation stream and the supplemental hydrogen stream in branch line 44b may be co-distributed in a common distributor to the interbed location at the intermediate inlet 46i. The intermediate inlet 46i may be in downstream communication with the fractionation section 14 and, in an aspect, with the side outlet 182o of the vacuum fractionation column 160.

The second fractionation stream comprising unconverted oil in the second recycle line 184 may be recycled to the first inlet 32i to the hydrocracking reactor 40 to be further hydrocracked over the first hydrocracking catalyst bed 42a and perhaps other hydrocracking catalyst beds 42 along with the hydrocarbon feed stream and the hydrogen stream and hydroisomerized over the first hydroisomerization catalyst bed 42b.

Figure 2:
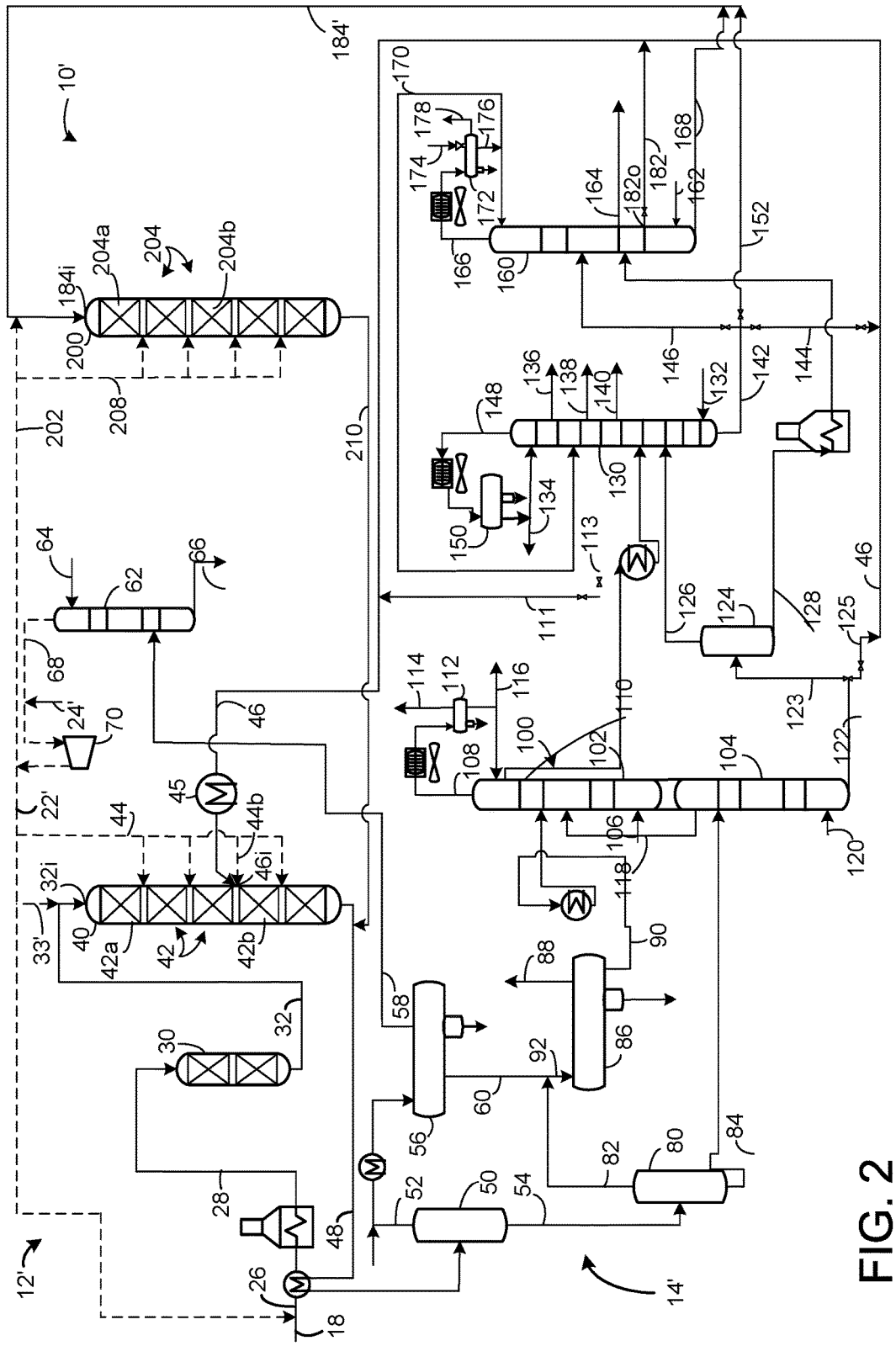
FIG. 2 is a schematic drawing of an alternative two-stage hydrocracking unit.

FIG. 2 shows an embodiment of the apparatus and process 10' that includes a second hydrocracking reactor 200 in the hydroprocessing unit 12'. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1 with the following exceptions.

The second hydrocracking reactor receives the second fractionation stream and a second hydrocracking hydrogen stream in a second hydrocracking hydrogen line 202 through a second inlet 184i in downstream communication with the fractionation section 14'. The second hydrocracking hydrogen stream in the second hydrocracking hydrogen line 202 is taken from the hydrogen stream in the hydrogen line 22'. A first hydrocracking hydrogen stream in the first hydrocracking hydrogen line 33' is taken from the hydrogen stream in the hydrogen line 22' provides hydrogen to the first hydrocracking reactor 40. The second fractionation stream comprises an unconverted oil stream from either the atmospheric fractionation column 130 and/or the vacuum fractionation column 160 in the second recycle line 184'. Accordingly, the second inlet 184i may be in downstream communication with an atmospheric bottoms line 142 of the atmospheric fractionation column 130 and/or the vacuum bottoms line 168 of the vacuum fractionation column 160.

The second hydrocracking reactor 200 comprises a plurality of catalyst beds 204. A second hydroisomerization catalyst bed 204a may be located in the second reactor 200. A second hydrocracking catalyst bed 204b may also be located in the second reactor 200. The second hydrocracking catalyst bed 204b may be located downstream of the second hydroisomerization catalyst bed 204a. In the second hydrocracking reactor 200, the second fractionated stream is hydroisomerized in the presence of a second hydrocracking hydrogen stream over the second hydroisomerization catalyst bed 204a to provide a second hydroisomerized stream. In the second hydrocracking reactor 200, the second fractionated stream is hydrocracked in the presence of the second hydrocracking hydrogen stream over the second hydrocracking catalyst bed 204b to provide a second hydrocracked stream. In an aspect, the second fractionation stream may also be a second hydroisomerized stream after it is hydroisomerized in the second hydroisomerization catalyst bed 204a and before it is hydrocracked in the second hydrocracking reactor 200. In an aspect, the upstream catalyst beds 204 in the second hydrocracking reactor 200 will suitably be hydroisomerization catalyst beds and the downstream catalyst beds 204 will be hydrocracking catalyst beds. A second hydrogen manifold 208 provides supplemental hydrogen streams to some or all of the catalyst beds 204 at the interbed locations. If a catalyst bed 204 comprises a hydroisomerization catalyst bed downstream of a hydrocracking catalyst bed 204 in the second hydrocracking reactor 200, a portion or all of the first fractionation stream from the first recycle line 46 may be used to quench the hydrocracked stream entering the hydroisomerization catalyst bed 204.

The second hydrocracked stream in line 210 may exit the second hydrocracking reactor 200. The second hydrocracked stream in line 210 may be joined to the first hydroisomerized stream in line 48 and be separated and fractionated in the fractionation section 14' with the first hydroisomerized stream.

EXAMPLE

Figure 3:
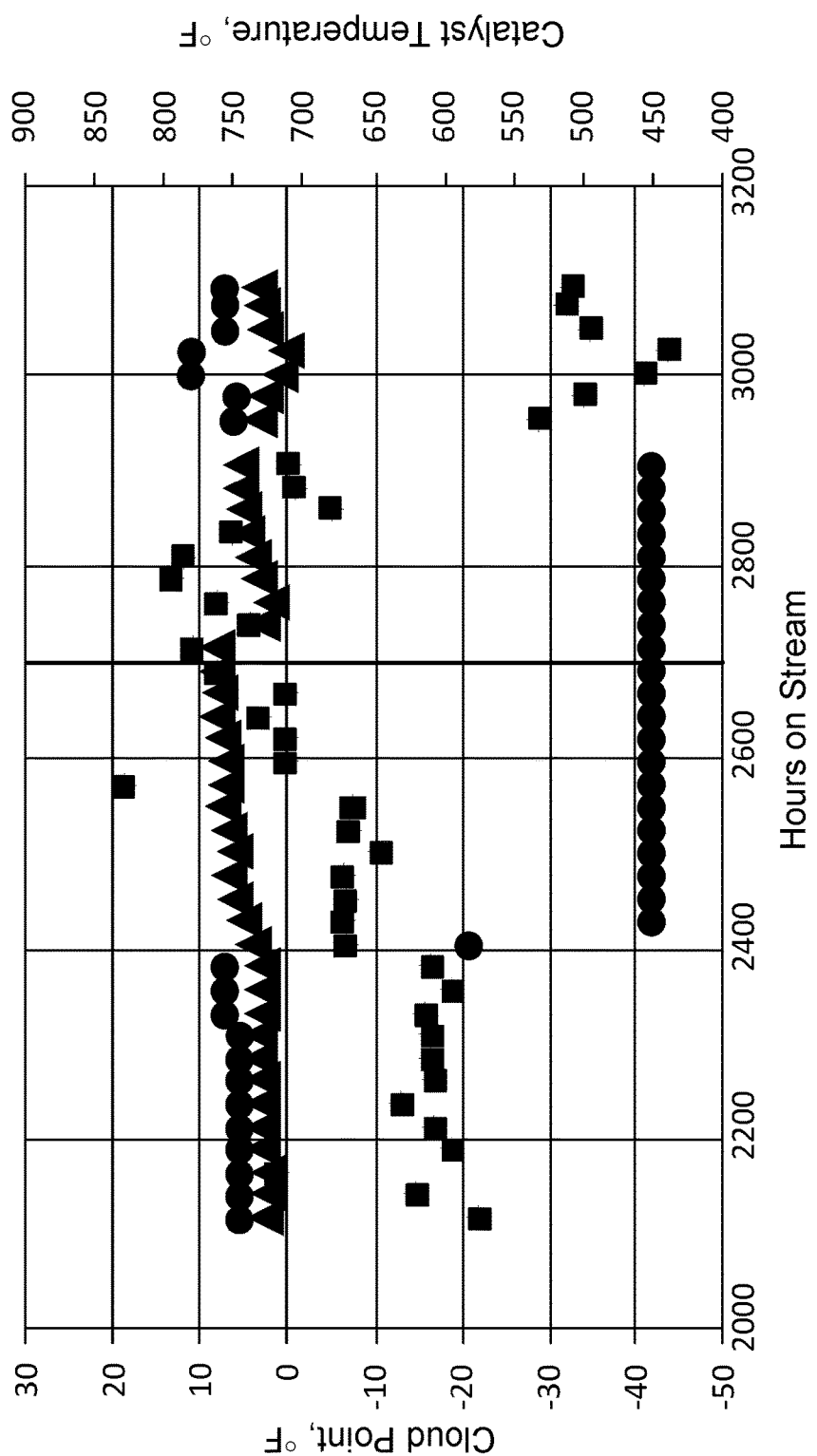
FIG. 3 is a plot of cloud point temperature and catalyst temperature over time.

FIG. 3 shows the effect of inactivating and reactivating hydroisomerization catalyst on cold flow properties, in this case Cloud Point. Two different VGO feeds were mixed with hydrogen and sequentially fed to a bed of hydrocracking catalyst and then to a bed of hydroisomerization catalyst in a pilot plant. The hydrocracking catalyst temperature is indicated by the triangles in FIG. 3. The hydroisomerization catalyst temperature is represented by the circles in FIG. 3. Catalyst temperature values are presented on the right vertical axis. Cloud point temperature values are represented by the squares and are presented on the left vertical axis. Hours on stream is presented on the horizontal axis. The vertical line at 2700 hours indicates the switching from one VGO feed to another VGO feed.

Hydrocracking catalyst temperature stayed generally between 700 and 800° F. during the entire run. Hydroisomerization catalyst temperature was maintained around 750° F. between 2100 and 2400 hours. During that time cloud point temperature stayed above −20° F. meaning that clouds do not form in the product diesel until the diesel temperature descends to or below the cloud point, in this case around −20° F. At 2400 hours, the hydroisomerization catalyst temperature was reduced to 585° F., at which time cloud point temperature rose to −5° F. Hydroisomerization catalyst temperature was allowed to cool to 450° F. resulting in cloud point staying at about −5 or −6° F. until 2550 hours at which time the cloud point spiked and fell to a higher stabilized cloud point temperature of 0° F. A new VGO feed was introduced at 2700 hours, and cloud point temperature rose to about 10° F. which is probably attributed to quality of the new feed because the hydroisomerization catalyst temperature was still at about 450° F. While the hydroisomerization catalyst was below 600° F., and particularly below 500 F, it was effectively inactive as shown by the significantly higher cloud point temperature of the produced diesel.

At after 2900 hours, the hydroisomerization catalyst temperature was increased to 750° F. The cloud point temperature immediately descended to −30° F. When the hydroisomerization catalyst temperature was increased to 775° F., cloud point temperature of the diesel product moved to below −40 F a superb quality.

We conclude that hydroisomerization catalyst can be operated with hydrocracking catalyst to improve cold flow properties of the hydrocracked diesel product. Moreover, the hydroisomerization catalyst temperature can be reduced to inactivate the hydroisomerization catalyst during warmer months when cold flow properties are less desired. Furthermore, when the warmer months are over, the same hydroisomerization catalyst can be reactivated by heating it up or not cooling it and the catalyst can begin to effectively hydroisomerized where it left off before it was cooled.

SPECIFIC EMBODIMENTS

While the following is described in conjunction with specific embodiments, it will be understood that this description is intended to illustrate and not limit the scope of the preceding description and the appended claims.

A first embodiment of the invention is a process for hydrocracking and hydroisomerizing a hydrocarbon stream comprising hydrocracking a hydrocarbon feed stream over a first hydrocracking catalyst bed to provide a hydrocracked stream; hydroisomerizing the hydrocracked stream over a first hydroisomerization catalyst bed to provide a hydroisomerized stream; fractionating the hydroisomerized stream in a fractionation section to provide a first fractionated stream; and recycling a first fractionated stream to the first isomerization catalyst bed to quench the hydrocracked stream. An embodiment of the invention is one, any or all of prior embodiments in this paragraph up through the first embodiment in this paragraph further comprising hydrocracking a second fractionated stream over the first hydrocracking catalyst bed. An embodiment of the invention is one, any or all of prior embodiments in this paragraph up through the first embodiment in this paragraph further comprising hydrocracking a second fractionated stream over a second hydrocracking catalyst bed to provide a second hydrocracked stream. An embodiment of the invention is one, any or all of prior embodiments in this paragraph up through the first embodiment in this paragraph wherein the first hydrocracking catalyst bed and the first hydroisomerization catalyst bed are located in a first reactor and the second hydrocracking catalyst bed is located in a second reactor. An embodiment of the invention is one, any or all of prior embodiments in this paragraph up through the first embodiment in this paragraph further comprising cooling the first fractionated stream to inactivate the first hydroisomerization catalyst bed. An embodiment of the invention is one, any or all of prior embodiments in this paragraph up through the first embodiment in this paragraph wherein the fractionation comprises stripping gases from the hydroisomerized stream to provide a stripped stream and recycling a portion of the stripped stream to the first isomerization catalyst bed as the first fractionated stream. An embodiment of the invention is one, any or all of prior embodiments in this paragraph up through the first embodiment in this paragraph wherein the fractionation comprises fractionating the hydroisomerized stream under vacuum and recycling a vacuum fractionated stream to the first isomerization catalyst bed as the first fractionated stream. An embodiment of the invention is one, any or all of prior embodiments in this paragraph up through the first embodiment in this paragraph wherein the first fractionated stream is taken as a side cut from a vacuum fractionation column. An embodiment of the invention is one, any or all of prior embodiments in this paragraph up through the first embodiment in this paragraph wherein the second fractionated stream is taken from a bottom of a fractionation column.

A second embodiment of the invention is a process for hydrocracking and hydroisomerizing a hydrocarbon stream comprising hydrocracking a hydrocarbon feed stream over a first hydrocracking catalyst bed in a first reactor to provide a hydrocracked stream; hydroisomerizing the hydrocracked stream over a first hydroisomerization catalyst bed in the first reactor to provide a hydroisomerized stream; fractionating a first effluent stream from the first reactor to provide a first fractionated stream and a second fractionated stream; recycling the first fractionated stream to the first isomerization catalyst bed in the first reactor to quench the hydrocracked stream; and hydrocracking the second fractionated stream over a second hydrocracking catalyst bed in a second reactor to provide a second hydrocracked stream. An embodiment of the invention is one, any or all of prior embodiments in this paragraph up through the second embodiment in this paragraph further comprising cooling the first fractionated stream to inactivate the first hydroisomerization catalyst bed. An embodiment of the invention is one, any or all of prior embodiments in this paragraph up through the second embodiment in this paragraph wherein the fractionation comprises stripping gases from the first effluent stream and recycling a portion of the stripped stream to the first isomerization catalyst bed as the first fractionated stream. An embodiment of the invention is one, any or all of prior embodiments in this paragraph up through the second embodiment in this paragraph wherein the fractionation comprises fractionating the first effluent stream under vacuum and recycling a vacuum fractionated stream to the first isomerization catalyst bed as the first fractionated stream. An embodiment of the invention is one, any or all of prior embodiments in this paragraph up through the second embodiment in this paragraph wherein the first fractionated stream is taken as a side cut from the vacuum fractionation column and the second fractionated stream is taken from a bottom of the vacuum fractionation column. An embodiment of the invention is one, any or all of prior embodiments in this paragraph up through the second embodiment in this paragraph wherein the fractionation comprises fractionating the first effluent stream and the first fractionated stream is taken as a side cut and the second fractionated stream is taken from a bottom of a fractionation column. An embodiment of the invention is one, any or all of prior embodiments in this paragraph up through the second embodiment in this paragraph further comprising fractionating another portion of the stripped stream to provide the second fractionated stream.

A third embodiment of the invention is an apparatus for hydrocracking and hydroisomerizing a hydrocarbon stream comprising a first hydrocracking reactor having a first inlet to the first hydrocracking reactor and an intermediate inlet to the first hydrocracking reactor downstream of the first inlet; a fractionation section downstream of the first hydrocracking reactor; and the intermediate inlet to the first hydrocracking reactor in downstream communication with the fractionation section. An embodiment of the invention is one, any or all of prior embodiments in this paragraph up through the third embodiment in this paragraph further comprising a second hydrocracking reactor having a second inlet to the second hydrocracking reactor in downstream communication with the fractionation section. An embodiment of the invention is one, any or all of prior embodiments in this paragraph up through the third embodiment in this paragraph wherein the fractionation section comprises a fractionation column and the second inlet is in downstream communication with a bottoms line of the fractionation column. An embodiment of the invention is one, any or all of prior embodiments in this paragraph up through the third embodiment in this paragraph wherein the intermediate inlet is in downstream communication with a side outlet of the fractionation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for hydrocracking and hydroisomerizing a hydrocarbon stream comprising:
    hydrotreating a hydrocarbon feed stream to provide a hydrotreated hydrocarbon feed stream;
    hydrocracking the hydrotreated hydrocarbon feed stream over a first hydrocracking catalyst bed to provide a hydrocracked stream;
    hydroisomerizing said hydrocracked stream over a first hydroisomerization catalyst bed to provide a hydroisomerized stream, wherein said hydroisomerizing is conducted at a lower temperature than said hydrocracking;
    fractionating said hydroisomerized stream in a fractionation section to provide a first fractionated stream; and
    recycling said first fractionated stream to said first hydroisomerization catalyst bed to quench said hydrocracked stream and provide a combined stream comprising said hydrocracked stream and said first fractionated stream;
    wherein said hydrocracked stream is fed to said first hydroisomerization catalyst bed bypassing said fractionation section.

2. The process of claim 1 further comprising hydrocracking a second fractionated stream over said first hydrocracking catalyst bed.

3. The process of claim 1 further comprising hydrocracking a second fractionated stream over a second hydrocracking catalyst bed to provide a second hydrocracked stream.

4. The process of claim 3 wherein said first hydrocracking catalyst bed and said first hydroisomerization catalyst bed are located in a first reactor and said second hydrocracking catalyst bed is located in a second reactor.

5. The process of claim 1 further comprising cooling said first fractionated stream to inactivate said first hydroisomerization catalyst bed.

6. The process of claim 1 wherein said fractionation comprises stripping gases from said hydroisomerized stream to provide a stripped stream and recycling a portion of said stripped stream to said first hydroisomerization catalyst bed as said first fractionated stream.

7. The process of claim 1 wherein said fractionation comprises fractionating said hydroisomerized stream under vacuum and recycling a vacuum fractionated stream to said first hydroisomerization catalyst bed as said first fractionated stream.

8. The process of claim 7 wherein said first fractionated stream is taken as a side cut from a vacuum fractionation column.

9. The process of claim 4 wherein said second fractionated stream is taken from a bottom of a fractionation column.

10. A process for hydrocracking and hydroisomerizing a hydrocarbon stream comprising:
hydrotreating a hydrocarbon feed stream to provide a hydrotreated hydrocarbon feed stream;
hydrocracking the hydrotreated hydrocarbon feed stream over a first hydrocracking catalyst bed in a first reactor to provide a hydrocracked stream;
hydroisomerizing said hydrocracked stream over a first hydroisomerization catalyst bed in said first reactor to provide a hydroisomerized stream, wherein said hydroisomerizing is conducted at a lower temperature than said hydrocracking;
fractionating a first effluent stream from said first reactor to provide a first fractionated stream and a second fractionated stream;
recycling said first fractionated stream to said first hydroisomerization catalyst bed in said first reactor to quench said hydrocracked stream; and
hydrocracking said second fractionated stream over a second hydrocracking catalyst bed in a second reactor to provide a second hydrocracked stream.

11. The process of claim 10 further comprising cooling said first fractionated stream to inactivate said first hydroisomerization catalyst bed.

12. The process of claim 10 wherein said fractionation comprises stripping gases from said first effluent stream and recycling a portion of said stripped stream to said first isomerization catalyst bed as said first fractionated stream.

13. The process of claim 10 wherein said fractionation comprises fractionating said first effluent stream under vacuum and recycling a vacuum fractionated stream to said first isomerization catalyst bed as said first fractionated stream.

14. The process of claim 13 wherein said first fractionated stream is taken as a side cut from said vacuum fractionation column and said second fractionated stream is taken from a bottom of said vacuum fractionation column.

15. The process of claim 10 wherein said fractionation comprises fractionating said first effluent stream and said first fractionated stream is taken as a side cut and said second fractionated stream is taken from a bottom of a fractionation column.

16. The process of claim 12 further comprising fractionating another portion of said stripped stream to provide said second fractionated stream.

* * * * *